US012746172B2

(12) United States Patent
Gregg, IV et al.

(10) Patent No.: US 12,746,172 B2
(45) Date of Patent: Sep. 29, 2026

(54) POWERED ORTHOSIS WITH COMBINED MOTOR AND GEAR TECHNOLOGY

(71) Applicant: Board of Regents, The University of Texas System, Austin, TX (US)

(72) Inventors: Robert D. Gregg, IV, Austin, TX (US); Hanqi Zhu, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 377 days.

(21) Appl. No.: 16/611,948

(22) PCT Filed: May 11, 2018

(86) PCT No.: PCT/US2018/032264
§ 371 (c)(1),
(2) Date: Nov. 8, 2019

(87) PCT Pub. No.: WO2018/209198
PCT Pub. Date: Nov. 15, 2018

(65) Prior Publication Data

US 2021/0085551 A1 Mar. 25, 2021

Related U.S. Application Data

(60) Provisional application No. 62/504,757, filed on May 11, 2017.

(51) Int. Cl.
*A61H 3/00* (2006.01)
*A61F 2/70* (2006.01)
(Continued)

(52) U.S. Cl.
CPC ................ *A61H 3/00* (2013.01); *A61F 2/70* (2013.01); *A61F 5/0102* (2013.01); *B25J 9/0006* (2013.01); *B25J 9/102* (2013.01); *B25J 19/0054* (2013.01); *A61F 2005/0155* (2013.01); *A61H 2201/1215* (2013.01); *A61H 2201/1472* (2013.01); *A61H 2201/164* (2013.01); *A61H 2201/50* (2013.01)

(58) Field of Classification Search
CPC ............................................ A61H 2201/1215
See application file for complete search history.

(56) References Cited

U.S. PATENT DOCUMENTS 5,226,874 A 7/1993 Heinz et al.
6,509,665 B1 1/2003 Nishiyama et al.
(Continued)

FOREIGN PATENT DOCUMENTS

WO 2009011682 1/2009

*Primary Examiner* — Jacqueline Woznicki
(74) *Attorney, Agent, or Firm* — Reising Ethington P.C.

(57) ABSTRACT

The present disclosure includes, in one embodiment, an orthosis device. The orthosis device, in one embodiment, includes an actuator housing, an electric motor contained within the actuator housing, the electric motor including a motor stator and a motor rotor forming an inner diameter, and the electric motor further having high output torque. The orthosis device according to this embodiment further includes a transmission including a gear system contained within the actuator housing, the gear system positioned within the inner diameter of the electric motor, and a body attachment coupled to an output of the gear system.

20 Claims, 13 Drawing Sheets

(51) Int. Cl.

| | |
|---|---|
| ***A61F 5/01*** | (2006.01) |
| ***B25J 9/00*** | (2006.01) |
| ***B25J 9/10*** | (2006.01) |
| ***B25J 19/00*** | (2006.01) |

(56) References Cited

U.S. PATENT DOCUMENTS

| | | | | |
|---|---|---|---|---|
| 7,125,388 | B1 * | 10/2006 | Reinkensmeyer | A63B 69/0064 601/5 |
| 2003/0064869 | A1 * | 4/2003 | Reinkensmeyer | A61H 3/008 482/8 |
| 2008/0000317 | A1 * | 1/2008 | Patton | F16H 19/06 623/32 |
| 2008/0071386 | A1 | 3/2008 | McBean et al. | |
| 2008/0249438 | A1 * | 10/2008 | Agrawal | A61H 1/0237 602/23 |
| 2012/0215358 | A1 * | 8/2012 | Gettings | B25J 19/023 294/213 |
| 2012/0283845 | A1 * | 11/2012 | Herr | A61F 2/6607 623/24 |
| 2014/0114437 | A1 | 4/2014 | Herr et al. | |
| 2015/0051528 | A1 | 2/2015 | Gilbert et al. | |
| 2015/0173993 | A1 | 6/2015 | Walsh et al. | |
| 2015/0216679 | A1 | 8/2015 | Lipsey et al. | |
| 2015/0216680 | A1 * | 8/2015 | Lipsey | A61F 2/586 623/24 |
| 2015/0226234 | A1 * | 8/2015 | Amundson | F15B 11/04 60/431 |
| 2015/0265427 | A1 | 9/2015 | Herr et al. | |
| 2016/0317375 | A1 * | 11/2016 | Simon | A61F 2/605 |
| 2018/0325713 | A1 * | 11/2018 | Gregg | A61F 5/0102 |
| 2020/0129314 | A1 * | 4/2020 | Herr | A61F 2/72 |
| 2025/0112537 | A1 * | 4/2025 | Abbott | B25J 9/0006 |

* cited by examiner

- Rated Power: 120 W
- Rated Speed: 626.154 rpm
- No Load Speed: 864.4 rpm
- Rated Torque: 2.19 Nm
- Armature Copper Loss: 26.44 W
- Core loss: 2.38 W
- Rated Efficiency: 83.31%
- Phase Current: 10.8 Arms
- Electrical Load: 208 A/cm
- Current Density: 8 A/mm$^2$

POWERED ORTHOSIS WITH COMBINED MOTOR AND GEAR TECHNOLOGY

CROSS-REFERENCE TO RELATED APPLICATION

This application is the National Stage of, and therefore claims the benefit of International Application No. PCT/US2018/032264 filed on May 11, 2018, entitled "POWERED ORTHOSIS WITH COMBINED MOTOR AND GEAR TECHNOLOGY," which was published in English under International Publication Number WO 2018/209198 on Nov. 15, 2018 and has a priority date of May 11, 2017 based on U.S. Provisional Application Ser. No. 62/504,757. Both of the above applications are commonly assigned with this National Stage application and are incorporated herein by reference in their entireties.

GOVERNMENT LICENSE RIGHTS

This invention was made with government support under HD080349 awarded by the National Institutes of Health. The government has certain rights in this invention.

TECHNICAL FIELD

This application is directed, in general, to limb powered orthoses and, more specifically, to limb powered orthoses with combined motor and gear technology.

BACKGROUND

Physical training is often needed for patients to relearn how to walk after a stroke. However, finite medical resources limit the frequency and availability of physical training. To address this, researchers are investigating powered lower-limb rehabilitation orthoses to relieve the repetitive and physically tasking duties of therapists, as well as to improve patient recovery efficacy. Currently, most lower-limb rehabilitation orthoses are stationary and only available in a small number of hospitals, due to high cost and large size. Personal mobile lower-limb orthoses that can be used in the clinic, at home or at work, among other places, are desirable for a variety of different reasons.

BRIEF DESCRIPTION

Reference is now made to the following descriptions taken in conjunction with the accompanying drawings, in which:

FIG. 1 is an orthosis device manufactured and designed in accordance with the present disclosure attached to a leg of a user;

FIGS. 2*a* and 2*b* illustrate various different stator core and winding designs;

Figure 6A:
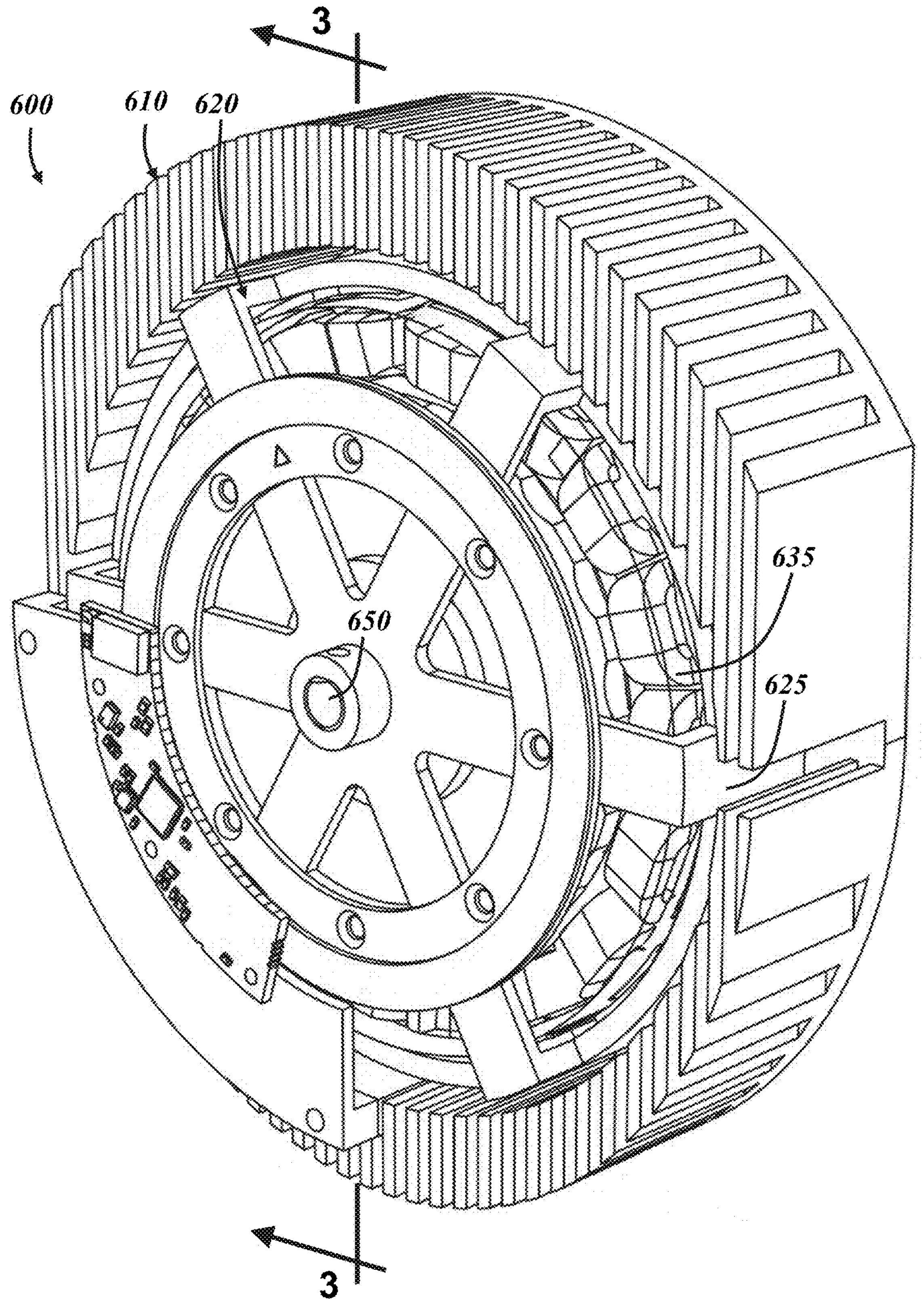
Figure 6B:
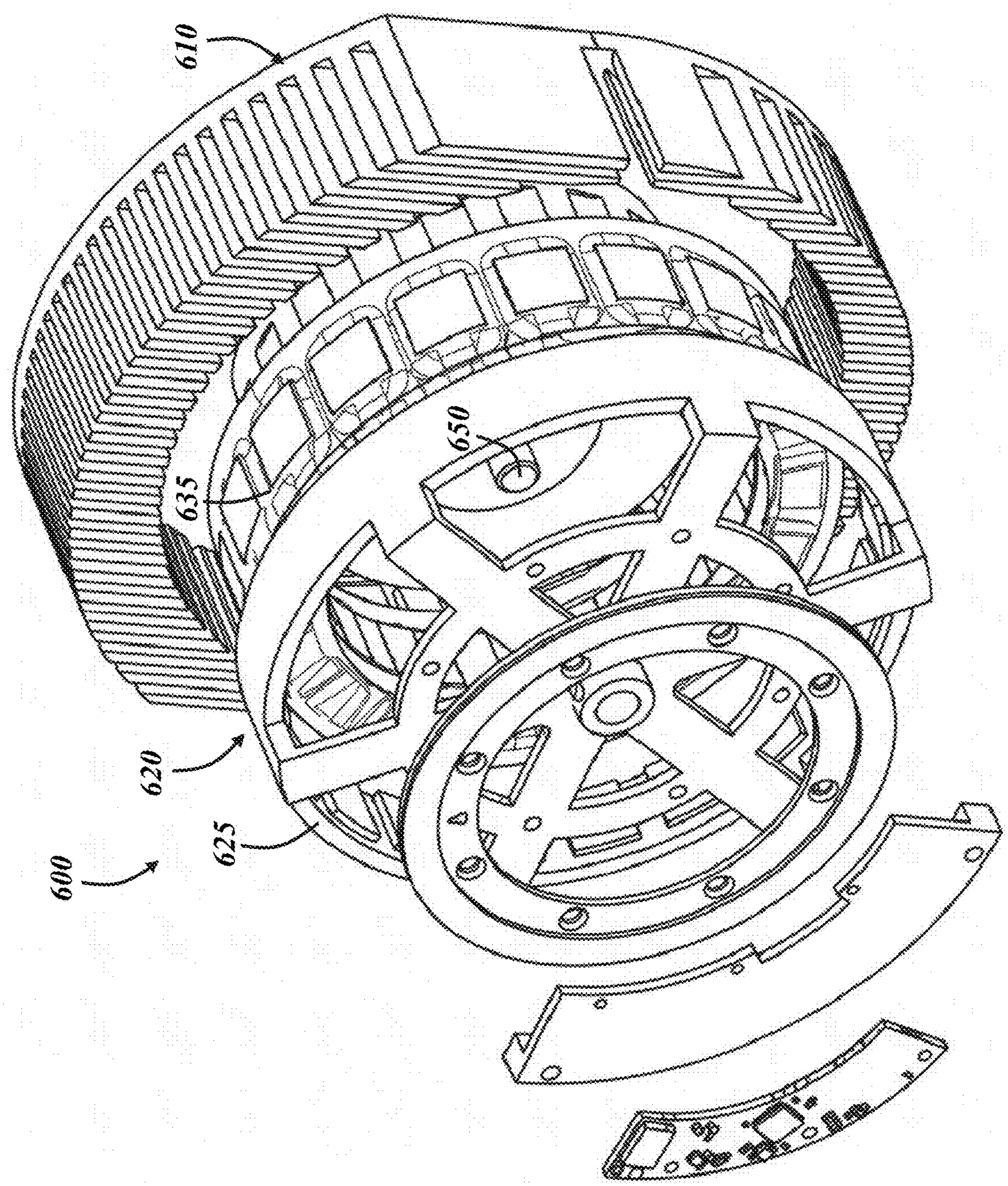
Figure 6C:
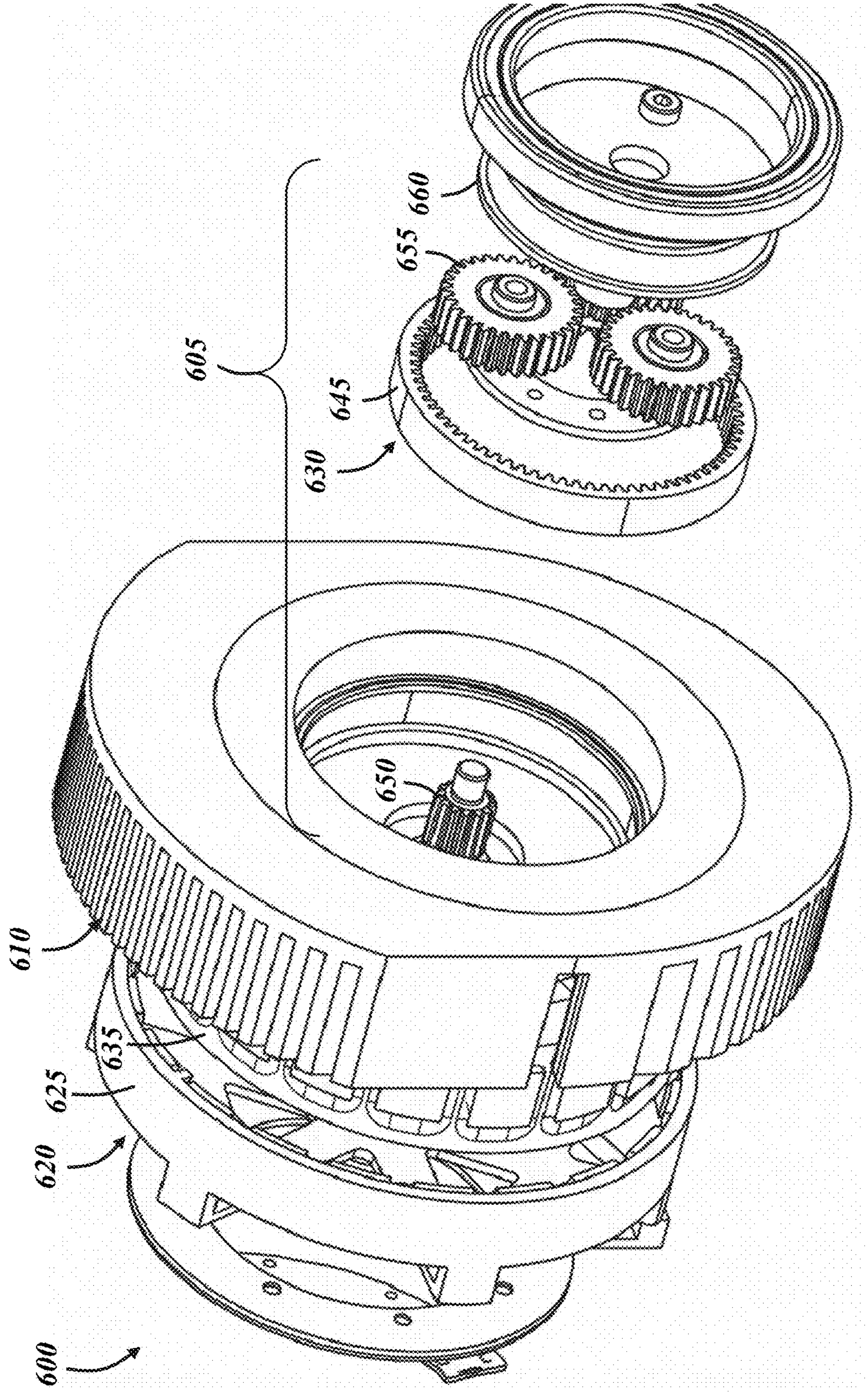
Figure 7:
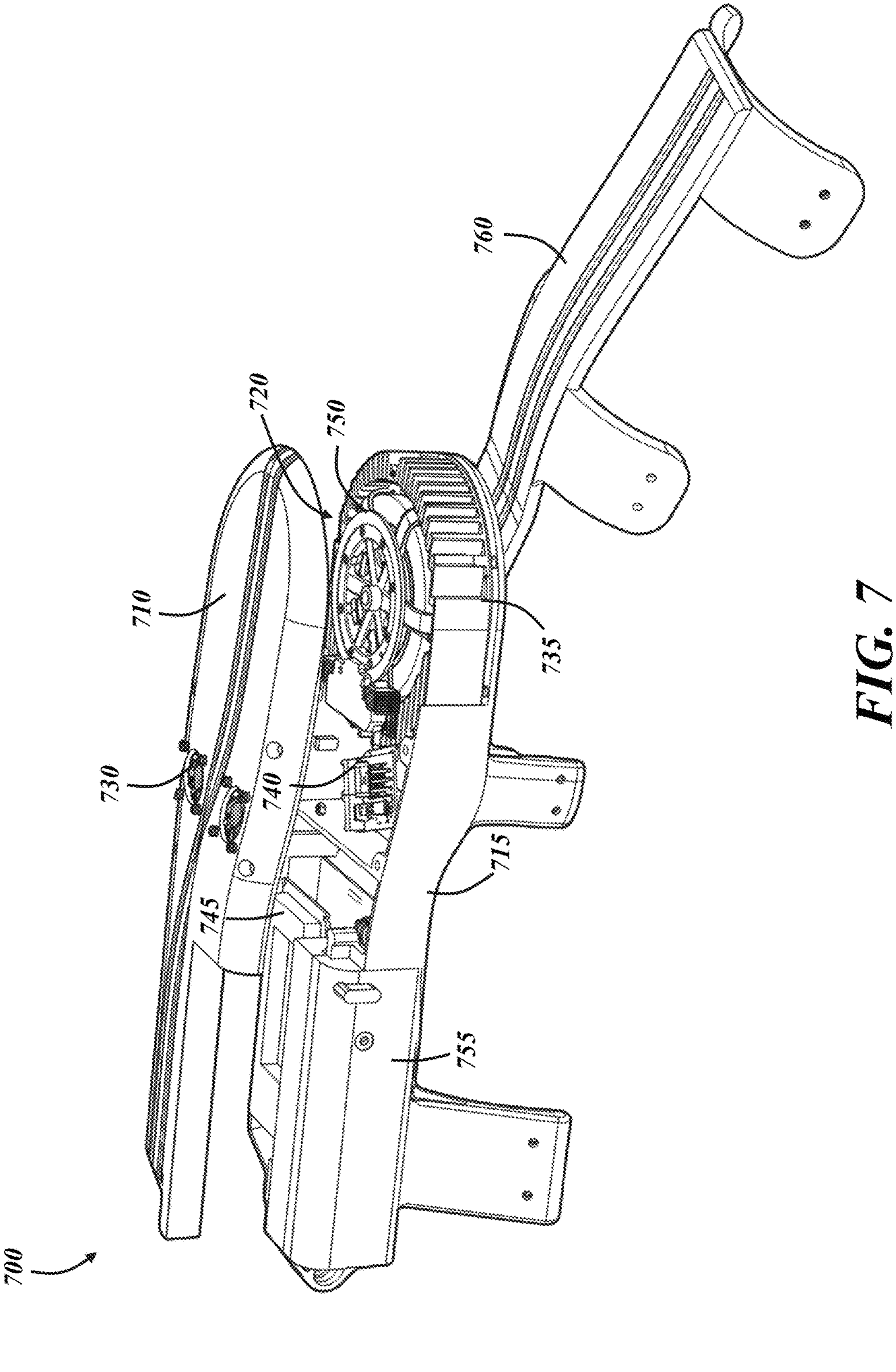
Figure 8A:
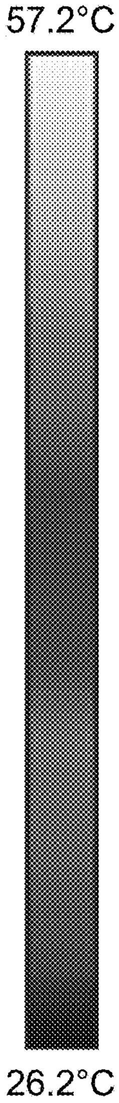
Figure 8A:
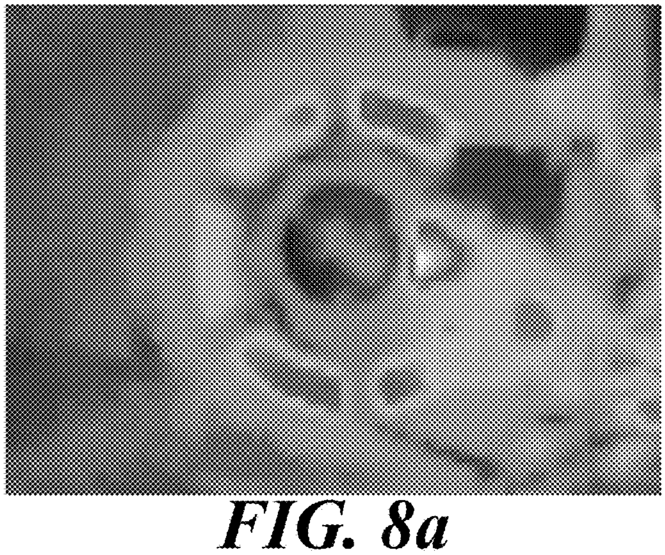
Figure 8B:
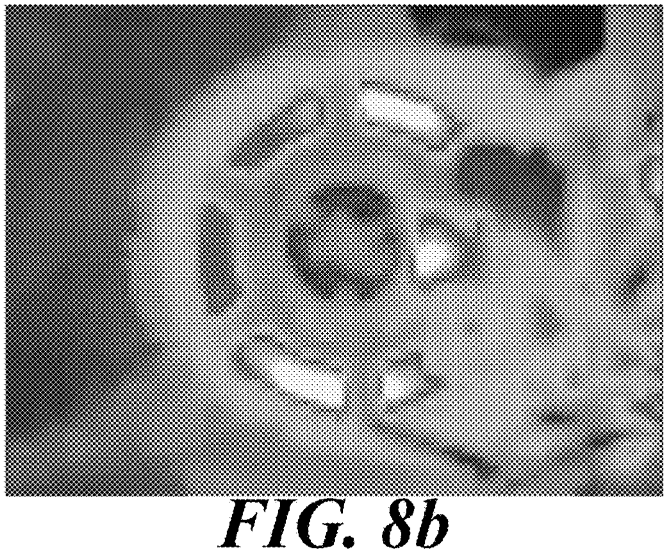
Figure 8C:
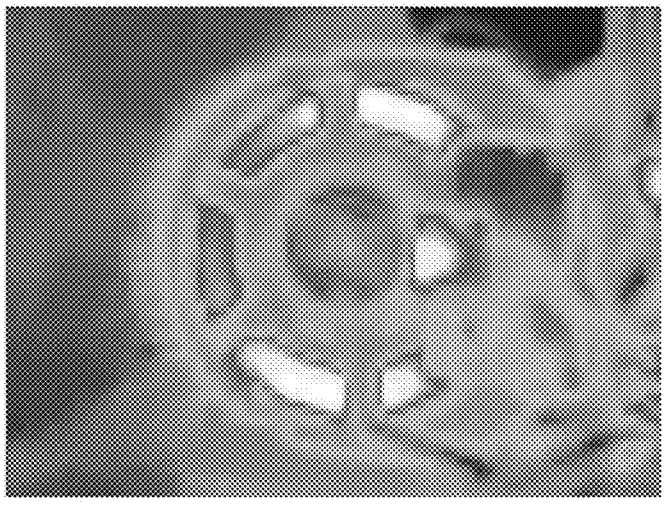
Figure 9:
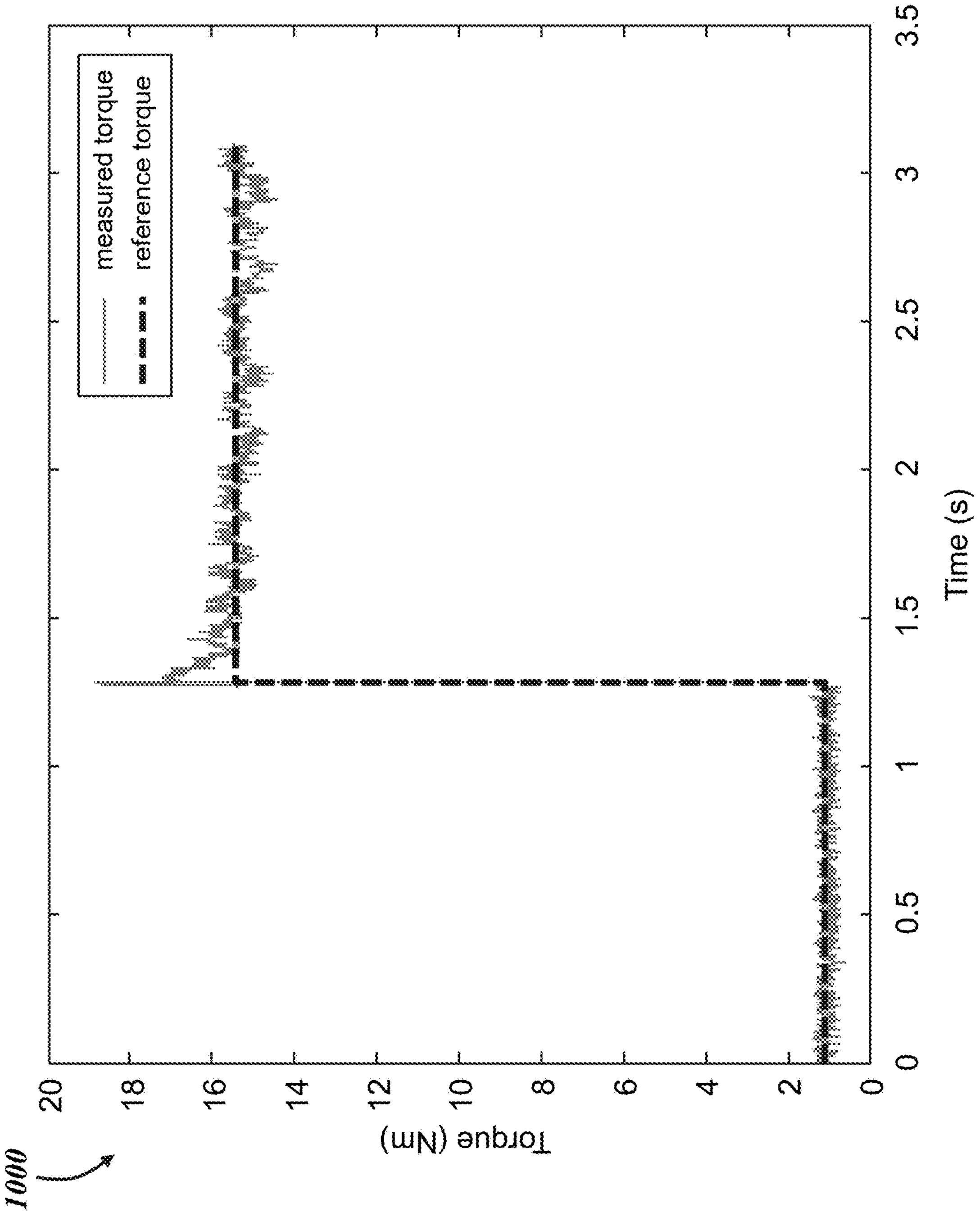
Figure 10:
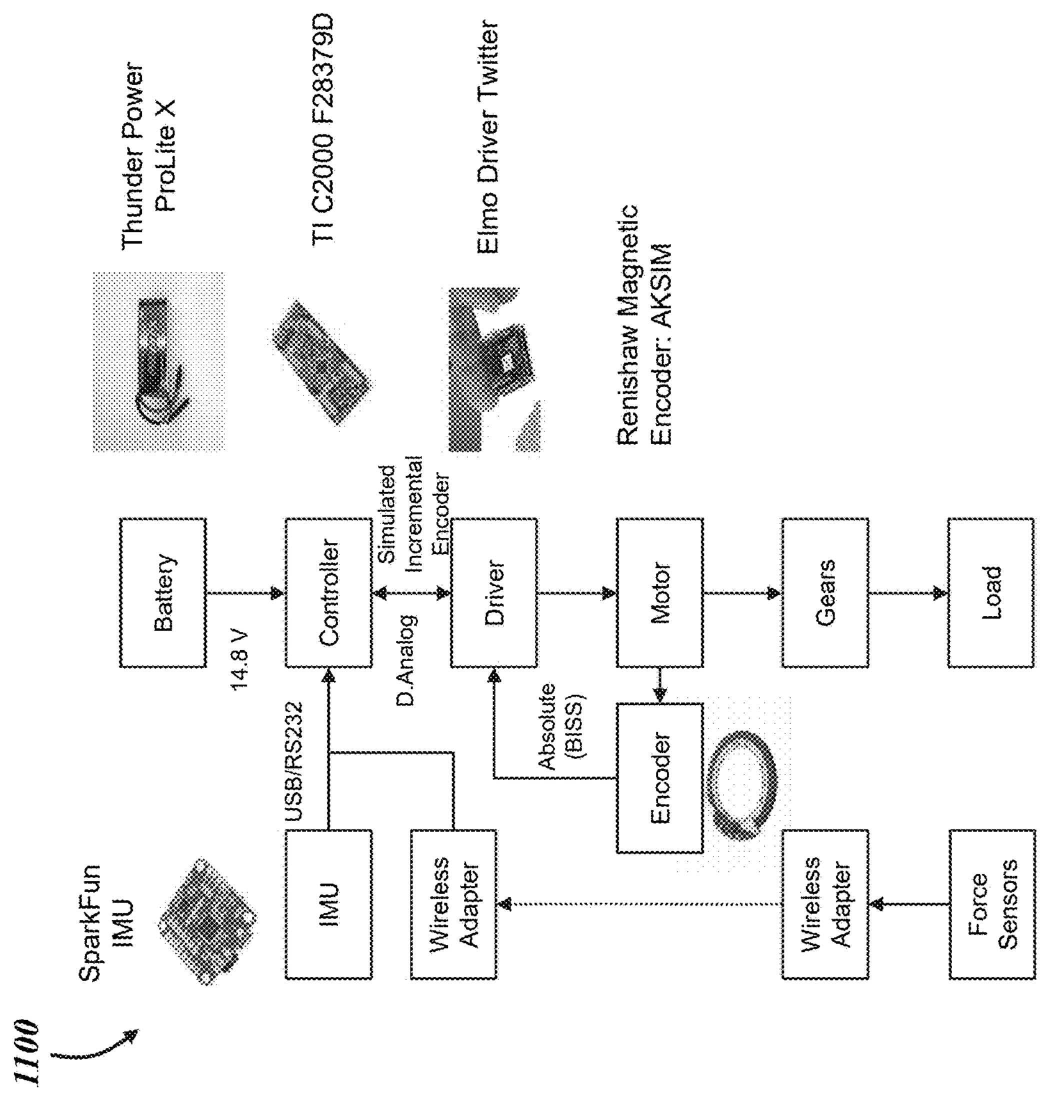
Figure 10:
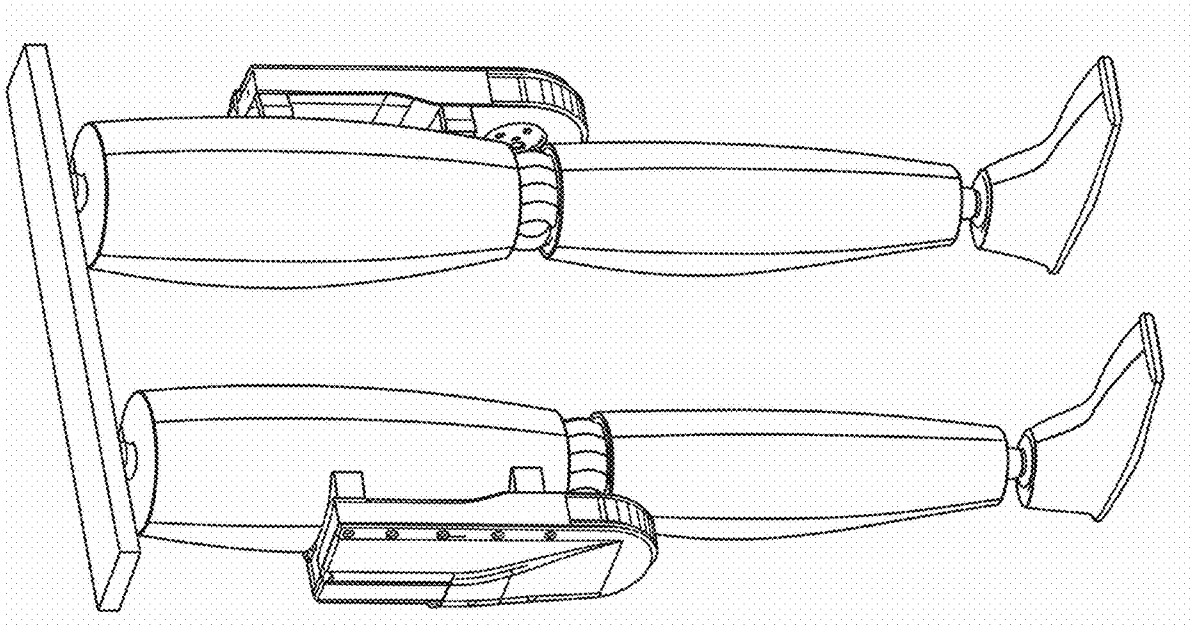

FIGS. 6*a*-6*c* illustrate an orthosis device manufactured in accordance with another embodiment of the disclosure;

FIG. 7 illustrates a substantially complete orthosis device with a top case removed;

FIGS. 8*a*-8*c* illustrate thermal images of a test actuator during operation;

FIG. 9 illustrates one example of measured actuator torque in accordance with the disclosure; and FIG. 10 illustrates one embodiment of an electrical system that might be used for an orthosis device manufactured in accordance with the disclosure.

DETAILED DESCRIPTION

Due to the high torque requirements of lower-limb joints, past research has focused on increasing the torque density of powered orthoses to provide enough output torque within an acceptable weight. Consequently, the combination of a high-speed motor and a high-ratio transmission, e.g., ball screw or harmonic drive, is common in traditional powered lower-limb orthoses. The present disclosure has recognized that the use of a high-ratio transmission results in high mechanical impedance, which means that the user cannot move their joints without help from the orthosis.

An orthosis is said to be backdrivable if users can drive their joints without a high resistive torque from the orthosis. Backdrivability may not be necessary for patients who cannot contribute to their walking gait, e.g., patients with spinal cord injuries. However, for patients who still have some control of their legs, a backdrivable orthosis can promote user participation and provide comfort during physical therapy. In particular, a mobile powered lower-limb orthosis for stroke rehabilitation purposes should be as mechanically transparent as possible. The present disclosure has further recognized that certain mobile powered lower-limb orthoses may be used to augment entirely healthy users, such as employees in the workforce or soldiers on a battlefield, among others.

The present disclosure, for the first time, details the design of a novel powered limb (e.g., knee) orthosis that achieves 1) high output torque with a low-ratio transmission (e.g., without a high-ratio transmission) and 2) precise torque control and backdrivability, entirely powered and contained within a single package. The present disclosure, again for the first time, achieves high continuous torque with low back-drive torque in a compact package by integrating several individual and combined technologies: 1) motor encapsulation technology, 2) a single stage gearbox built into the inner diameter of the motor, 3) a forced air cooling system, 4) a heat sink, 5) a transmission that does not include a clutch, 6) a non-variable transmission. All the above features dramatically improve the powered orthosis performance in clinic application and daily life use.

For the purpose of the present disclosure and claims, a high output torque motor has a peak output torque (e.g., measured over a 1 second time period) of at least about 1.0 Nm. Similarly, for the purpose of the present disclosure and claims, a very high output torque motor has a peak output torque (e.g., measured over a 1 second time period) of at least about 1.5 Nm, and an extremely high output torque motor has a peak output torque (e.g., measured over a 1 second time period) of at least about 2.0 Nm. Also, for the purpose of the present disclosure and claims, an excessively high output torque motor has a peak output torque (e.g., measured over a 1 second time period) of at least about 4.0 Nm.

For the purpose of the present disclosure and claims, a high torque density motor has a torque density (e.g., a measure of the peak torque output divided by the motor's stator and rotor weight) of at least about 3.3 Nm/kg. Similarly, for the purpose of the present disclosure and claims, a very high torque density motor has a torque density (e.g., a measure of the peak torque output divided by the motor's stator and rotor weight) of at least about 5.0 Nm/kg, and an extremely high torque density motor has a torque density (e.g., a measure of the peak torque output divided by the motor's stator and rotor weight) of at least about 6.7 Nm/kg. Also, for the purpose of the present disclosure and claims, an excessively high torque density motor has a torque density (e.g., a measure of the peak torque output divided by the motor's stator and rotor weight) of at least about 13.3 Nm/kg.

Additionally, for the purpose of the present disclosure and claims, a low-ratio transmission is a transmission with a ratio of 32:1 or less. Similarly, for the purpose of the present disclosure and claims, a very low-ratio transmission is a transmission with a ratio of 24:1 or less, and an extremely low-ratio transmission is a transmission with a ratio of 16:1 or less. Additionally, for the purpose of the present disclosure and claims, an excessively low-ratio transmission is a transmission with a ratio of 12:1 or less.

Similarly, for the purpose of the present disclosure and claims, a device that is user backdrivable is a device wherein its static torque (e.g., minimum backdrive torque to begin motion of the motor shaft) is less than about 20 Nm. Likewise, for the purpose of the present disclosure and claims, a device that is very user backdrivable is a device wherein its static torque (e.g., minimum backdrive torque to begin motion of the motor shaft) is less than about 5 Nm, and a device that is extremely user backdrivable is a device wherein its static torque (e.g., minimum backdrive torque to begin motion of the motor shaft) is less than about 2.5 Nm. Also, for the purpose of the present disclosure and claims, a device that is excessively backdrivable is a device wherein its static torque (e.g., minimum backdrive torque to begin motion of the motor shaft) is less than about 2.0 Nm.

Figure 1:
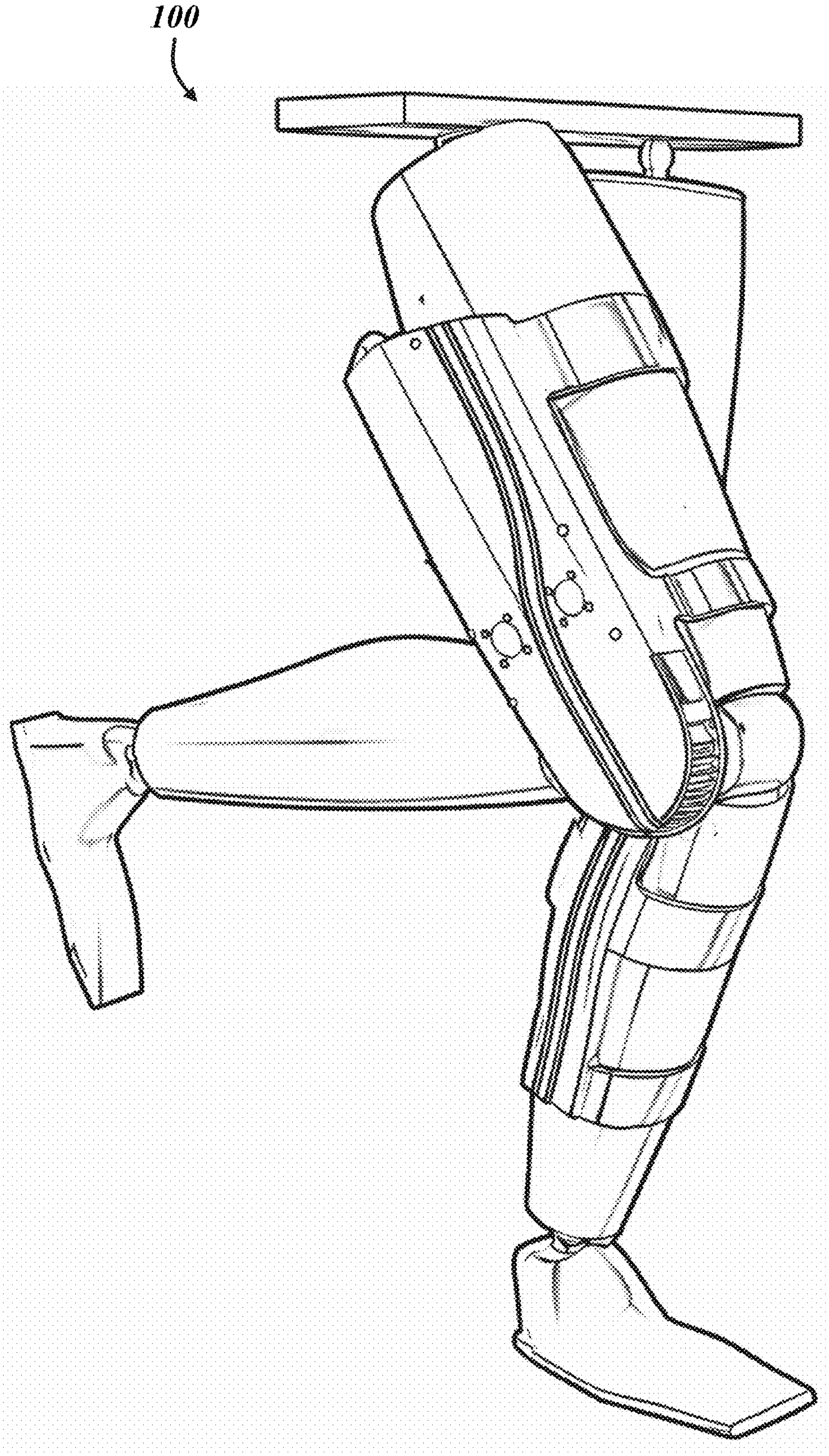

Turning to FIG. 1, illustrated is a depiction of an orthosis device 100 manufactured and designed in accordance with the present disclosure attached to a leg of a user. As can be seen, the orthosis device is entirely self-contained. The term self-contained, as used in this context, means that all the parts (e.g., including the necessary controllers and power) necessary for the orthosis to operate are contained within the same unit. Thus, to be self-contained, there are no external power supplies, control devices, etc. Accordingly, the orthosis device 100, such as that shown in FIG. 1, is collectively cheaper to manufacture, more effective, more comfortable (e.g., backdrivable), more user friendly, and lighter than all previously known related orthosis devices.

In accordance with the disclosure, electrical motor encapsulation technology may be used in the orthosis design. For example, to increase the electric motor's torque density, a high thermal conductivity material may be used to fill the gap between the windings and core of the stator. As a result, the heat from the winding can transfer to the environment easier. As is only now known, the orthosis' continuous torque output and peak torque output are improved by using this technology.

Figure 2A:
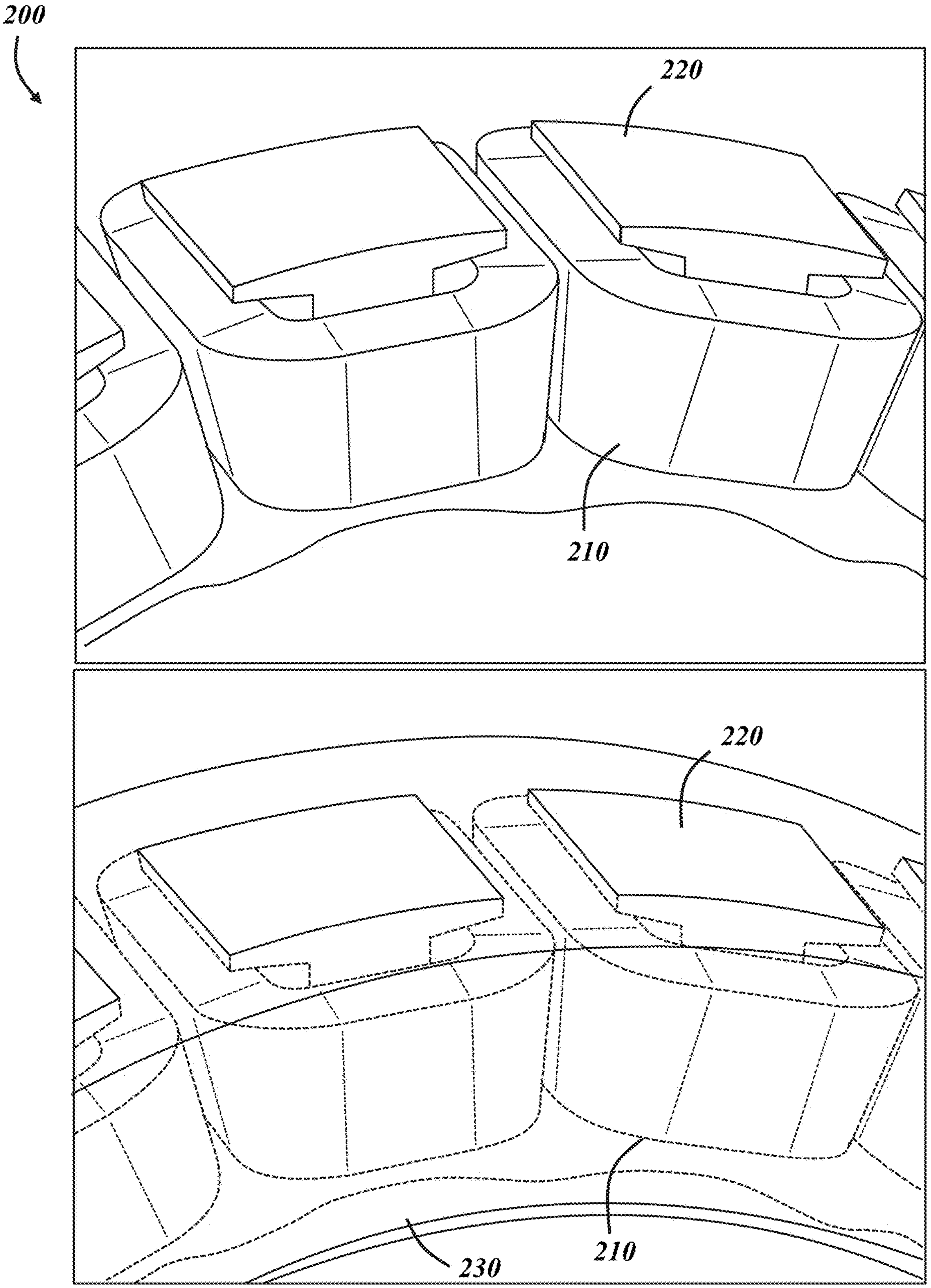
Figure 2B:
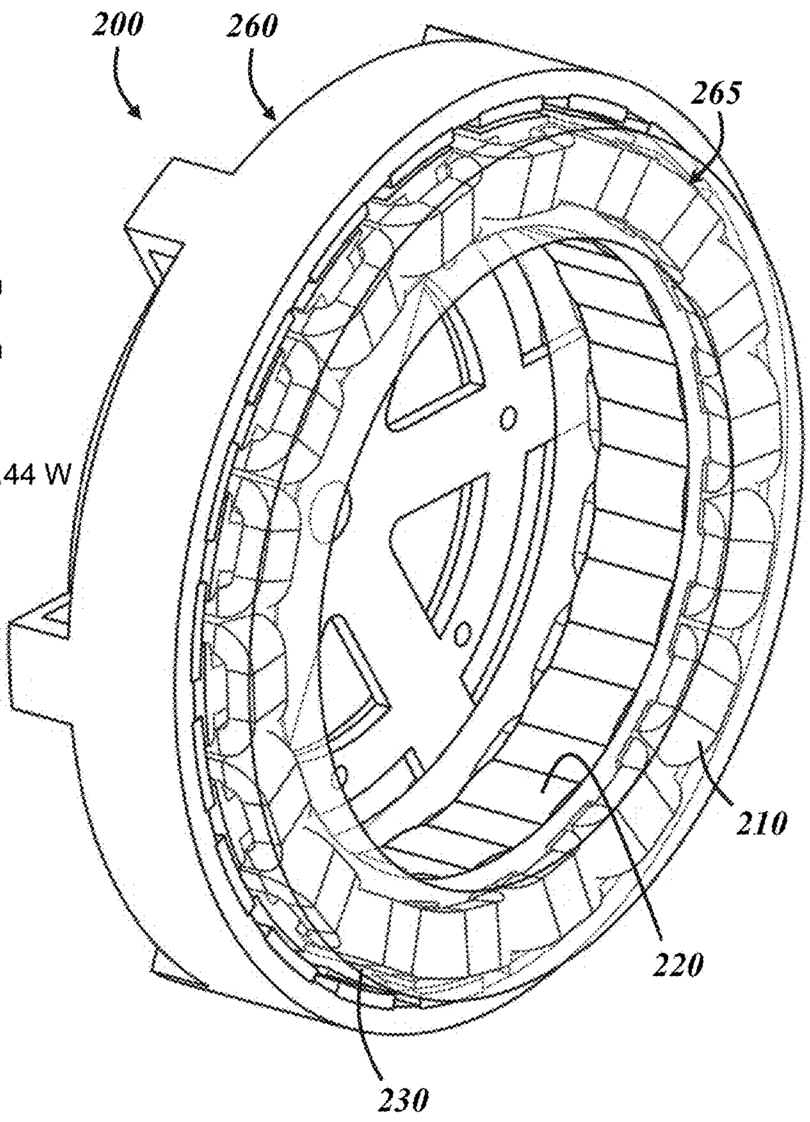

Turning briefly to FIG. 2*a*, illustrated is a portion of a motor design 200 with and without the aforementioned encapsulation technology. In the leftmost illustration (e.g., the one without the encapsulation technology), the heat generated in the stator windings 210 has to transfer from the stator windings 210 to the stator cores 220 though a gap filled with insulation. The insulation normally has very poor thermal conductivity, which is detrimental to the ability of the stator cores 220 and stator windings 210 to dissipate heat. However, in the rightmost illustration, the stator cores 220 and the stator windings 210 are covered by an encapsulation 230 (e.g., high thermal conductivity material in one embodiment). In this instance, the heat generated from the stator windings 210 is more easily transferred to the environment. Turning briefly to FIG. 2*b*, illustrated is an alternative view of the motor design 200, including a rotor 260 and a stator 265 with the encapsulation technology 230.

Figure 3:
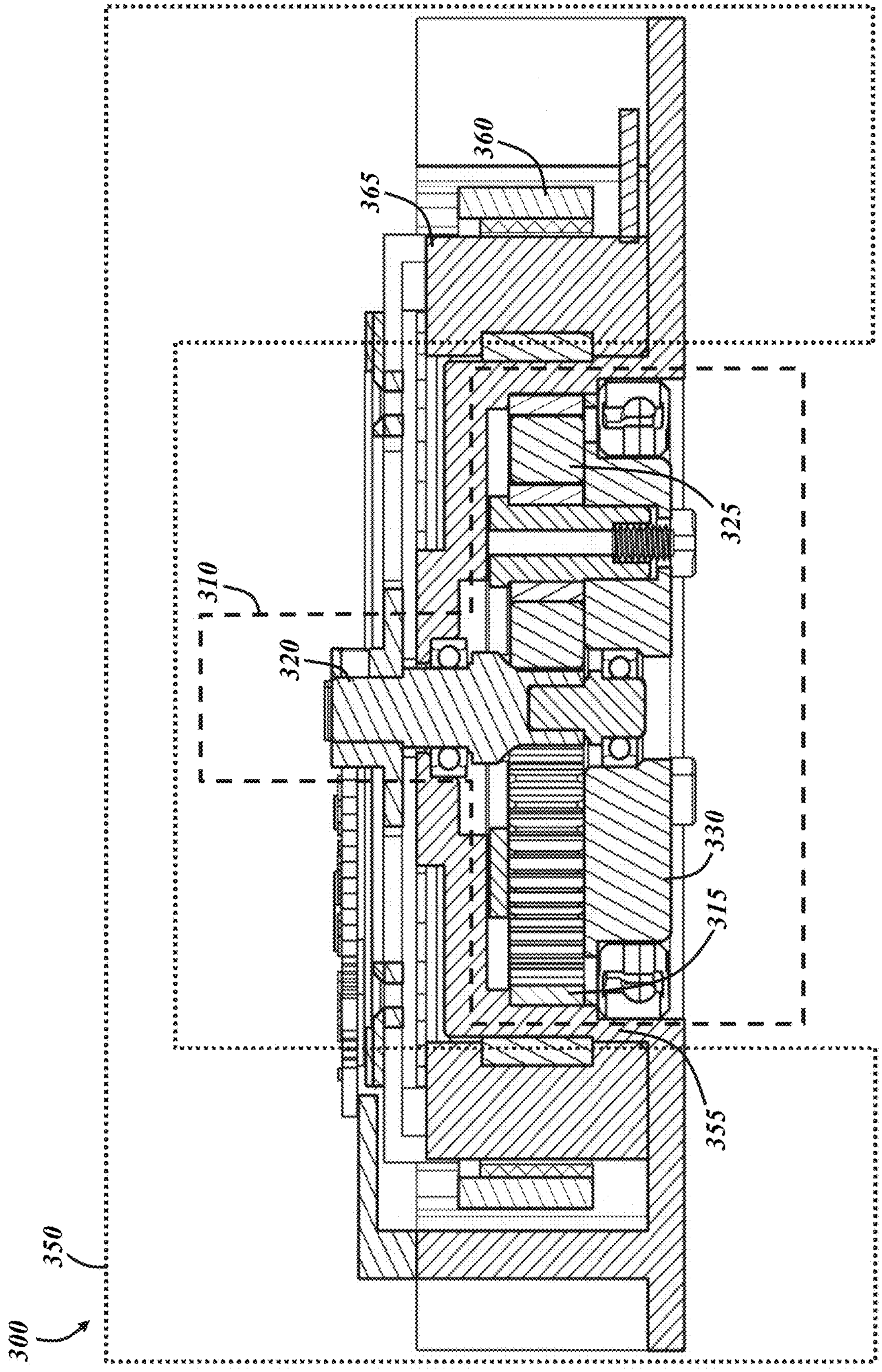
FIG. 3 illustrates a gear system contained within an electric motor.

In accordance with another aspect of the disclosure, the motor/gear system 300 is formed as a single unit. For example, as shown in FIG. 3, the gear system 310 (e.g., entire gear system in one embodiment, including the ring gear 315, sun gear 320, planet gear 325 and planet gear carrier 330) of a gear-reduction transmission may be contained within the electric motor 350 (e.g., motor housing 355, rotor 360 and stator 365). By using the outer electric rotor motor 350, a single stage planetary gear system may be built inside the motor stator. In this example, the sun gear 320 is the input of the gear-reduction transmission, the motor rotor 360 is directly connected to the input of the transmission, and the ring gear 315 is built inside the stator 365. Accordingly, the motor/gear system 300 illustrated in FIG. 3, or at least the outer diameter of the rotor 360, is under 150 mm (e.g., under 110 mm in one embodiment).

Figure 4:
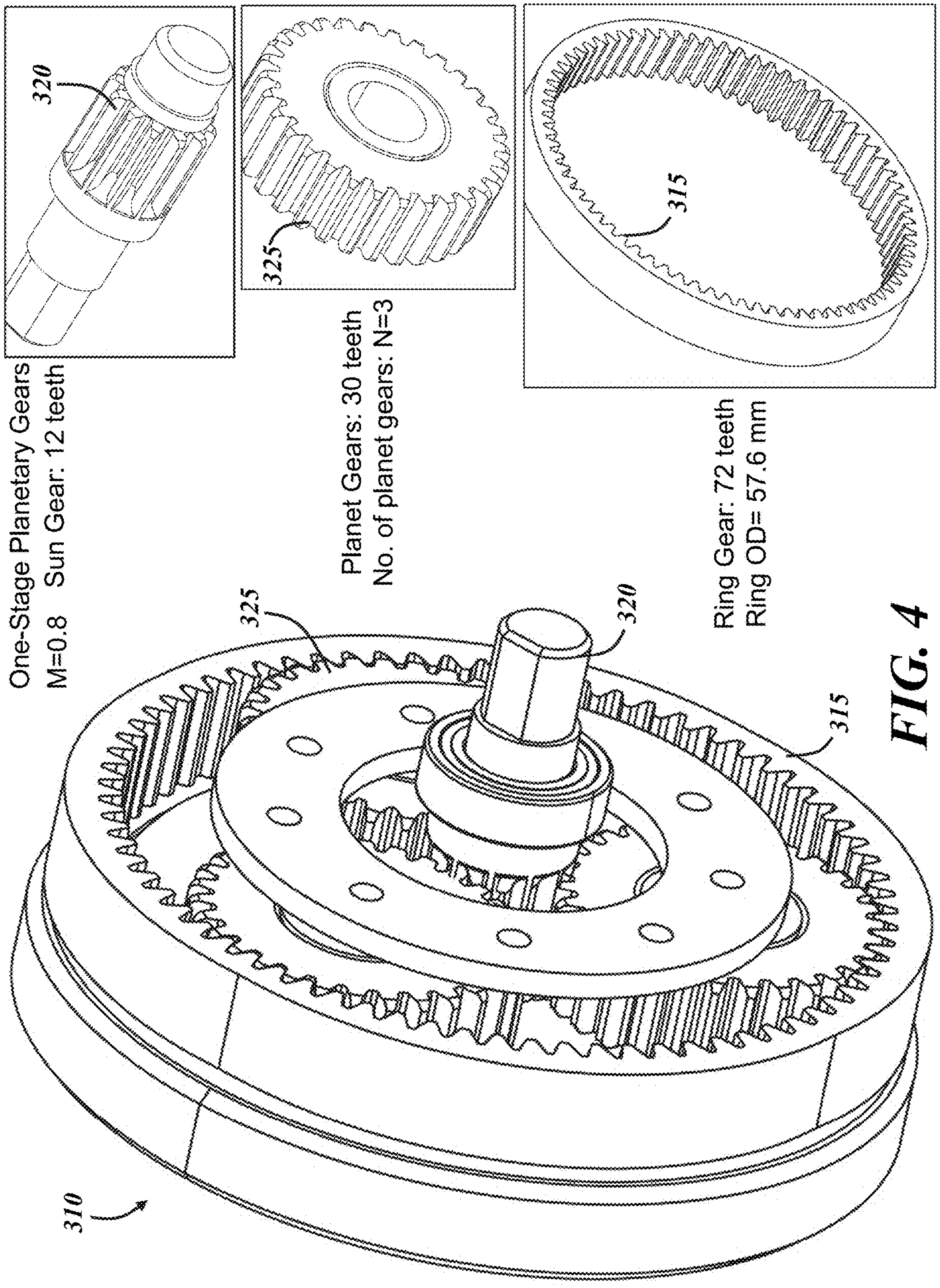
FIG. 4 illustrates an additional view of the gear system.

Turning briefly to FIG. 4, illustrated is an additional view of the gear system 310. As can be readily noticed, the gear system 310 may be a planetary gear system. Additionally, in one embodiment, the electric motor 350 is designed to have a peak torque of approximately 4.2 Nm, resulting in an excessively high output torque motor.

Figure 5:
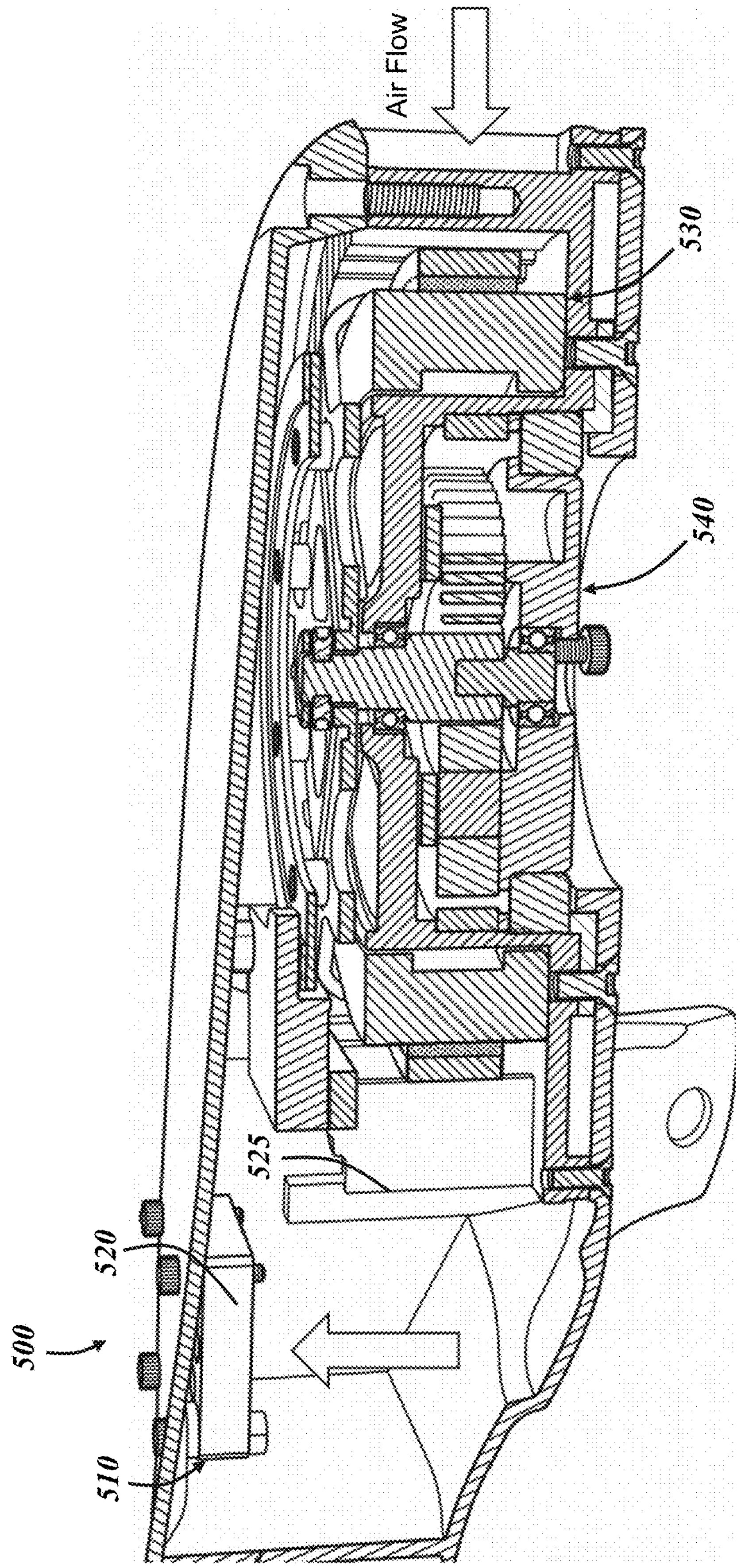
FIG. 5 illustrates one embodiment of a forced air cooling system.

In accordance with another aspect of the disclosure, a forced air cooling system may be used to assist in removing any heat from the orthosis device. Turning to FIG. 5, illustrated is one embodiment of a forced air cooling system 510 that might be used in an orthosis device 500. As is illustrated in FIG. 5, the forced air cooling system 510 of the orthosis device 500 may include one or more fans 520 and an actuator 525 that draw and/or push ambient air across the electric motor 530 and/or gear system 540, thereby cooling the orthosis device 500. In one embodiment, the air is drawn substantially upward (e.g., as it relates to gravity), thereby taking advantage of convection to assist with any heat removal.

Turning to FIGS. 6*a*, 6*b*, and 6c, illustrated is an alternative embodiment of an orthosis device 600 manufactured in accordance with the disclosure employing a heat sink 610 (e.g., a fin based heat sink) to further remove the necessary heat. In the illustrated embodiment, the fins of the heat sink are designed to run substantially upward (e.g., as it relates to gravity), thereby again taking advantage of convection to assist with the heat removal. The orthosis device 600 illustrated in FIGS. 6*a*-6*c* further illustrates the electric motor 620, including the rotor 625 and stator 635, being surrounded by the heat sink 610, and furthermore a transmission 605 including the gear system 630, which includes the ring gear 645, sun gear 650, planet gears 655, and planet gear carrier 660, the gear system being surrounded by the electric motor 620, as discussed above.

Turning to FIG. 7, illustrated is a depiction of a substantially complete orthosis device 700, with a top case 710 removed from the enclosure 715, thereby exposing the various different features thereof. As can be readily viewed, each of the electric motor 720 (e.g., actuator), gear system 725, heat removal system (e.g., fans 730 and/or heat sink 735), motor driver 740, electrical controller 745, encoder 750 and power source 755 (e.g., batteries) are housed within the same enclosure 715 under the top case 710. The orthosis device 700 further includes a body attachment (e.g., shank attachment) 760. Accordingly, the orthosis device 700 illustrated in FIG. 7 is a self-contained unit.

One example of an assembled actuator was validated with several experiments to demonstrate its continuous current, torque step response, torque bandwidth, and backdrive torque. The actuator was mounted to a test platform that comprised a rotational torque sensor (TRS605, FUTEK Advanced Sensor Technology, Inc. in the example test) coupled to a magnetic powder brake (351 Eleflex, Re Controlli Industriali in the example test). A thermal camera (C2 Compact Thermal Imaging System, FLIR in the example test) monitored the surface temperature of the actuator's motor. The first three properties were tested with the actuator's output shaft mechanically fixed by the powder brake with the Futek torque sensor in the middle. The backdrivability test was conducted with the actuator's output shaft coupled to a torque wrench (03727A ¼-inch Drive Beam Style, Neiko, in the example test).

A test actuator including the motor 200 of FIG. 2*b* and the gear system 310 of FIG. 4 was designed to accommodate a continuous active current of about 13 Amps, which relates to the output torque of the actuator. The continuous current can be held over long periods of time and therefore relates to the steady-state thermal dissipation properties of the test actuator. During this test, the test actuator was driven with an active current of about 13 Amps for 30 min while the thermal camera measured the surface temperature of the actuator. Surface temperature measurements were taken at 3 min (about 45.3 degrees C.), 15 min (about 53.9 degrees C.), and 30 min (about 57.2 degrees C.), which were below the safety specifications for protecting the motor's windings (preferably less than about 100 deg. C). The thermal images for 3 min., 15 min., and 30 min., respectively, are shown in FIGS. 8*a*, 8*b*, and 8c.

The torque step response demonstrates the high output torque of the actuator as well as its bandwidth. With the output shaft mechanically fixed, the actuator was commanded to output a step torque profile going from a preload of about 0.5 Nm to about 15 Nm, maintaining 15 Nm for about 2 seconds, and then going back to about 0.5 Nm. Note that an actuator output torque of about 15 Nm may correspond to a motor torque of about 2.14 Nm (before the transmission). One example of the measured actuator torque 1000 is shown in FIG. 9. These test results were imported into the MATLAB System Identification Toolbox to generate a model of the system. From this model the torque bandwidth frequency was estimated to be greater than about 61 Hz, which greatly exceeds the bandwidth of human walking.

The term static backdrive torque, as used herein, means the minimum torque required to overcome the static friction of the actuator to initiate motion of its output shaft. A torque was manually applied to the output shaft of the actuator through a torque wrench and gradually increased until rotation began. At this point the torque wrench measured less than about 0.5 Nm of static backdrive torque.

Turning briefly to FIG. 10, illustrated is one embodiment of an electrical system 1100 that might be used for an orthosis device, such as any of those discussed above.

Those skilled in the art to which this application relates will appreciate that other and further additions, deletions, substitutions and modifications may be made to the described embodiments.

What is claimed is:

1. An orthosis device, comprising:

an actuator housing;

an electric motor contained within the actuator housing, the electric motor including a motor stator and a motor rotor forming an inner diameter, and the electric motor further having high output torque;

a gear-reduction transmission including a gear system contained within the actuator housing, the gear system positioned within the inner diameter of the electric motor and the motor rotor being directly connected to an input of the transmission; and a body attachment coupled to an output of the gear system, wherein a combination of the electric motor and the transmission, and how they engage one another, enable the orthosis device to be user backdrivable such that a static backdrive torque of the device at the output of the gear system is less than 20 Nm and is a minimum backdrive torque to begin motion of the motor rotor.

2. The orthosis device of claim 1, wherein the gear system is a single stage gear system.

3. The orthosis device of claim 1, further including high thermal conductivity material substantially surrounding cores and windings of the stator.

4. The orthosis device of claim 1, further including a forced air cooling system contained within the actuator housing.

5. The orthosis device of claim 1, further including a heat sink at least partially surrounding the electric motor.

6. The orthosis device of claim 1, wherein the transmission is an excessively low-ratio transmission.

7. The orthosis device of claim 1, wherein the transmission has a ratio ranging from about 8:1 to about 3:1.

8. The orthosis device of claim 1, wherein the transmission has a ratio of about 7:1.

9. The orthosis device of claim 1, wherein the gear system is a planetary gear system.

10. The orthosis device of claim 1, wherein the transmission does not include a clutch or is not a variable transmission.

11. The orthosis device of claim 1, further including a motor encoder located within the actuator housing and associated with the electric motor.

12. The orthosis device of claim 1, wherein the actuator housing, electric motor, gear system, and power source form part of a self-contained unit.

13. The orthosis device of claim 1, wherein the electric motor has an extremely high output torque.

14. The orthosis device of claim 1, wherein the electric motor has an excessively high output torque.

15. The orthosis device of claim 1, wherein the orthosis device is very user backdrivable.

16. The orthosis device of claim 1, wherein the orthosis device is extremely user backdrivable.

17. The orthosis device of claim 1, wherein the orthosis device is excessively user backdrivable.

18. The orthosis device of claim 1, wherein the electric motor has a very high output torque, the transmission is an extremely low-ratio transmission, and the orthosis device is very user backdrivable.

19. The orthosis device of claim 1, wherein the stator is located within an inner diameter of the rotor.

20. The orthosis device of claim 1, wherein the gear system is a planetary gear system having a sun gear as the input of the transmission and planet gears that revolve around the sun gear when the sun gear rotates with respect to the stator.

* * * * *